(12) United States Patent
Hüttlin

(10) Patent No.: US 7,802,376 B2
(45) Date of Patent: Sep. 28, 2010

(54) APPARATUS FOR TREATING PARTICULATE MATERIAL

(76) Inventor: Herbert Hüttlin, Rümminger Strβfle 15, 79539 Lörrach (DE)

( * ) Notice: Subject to any disclaimer, the term of this patent is extended or adjusted under 35 U.S.C. 154(b) by 745 days.

(21) Appl. No.: 11/267,518

(22) Filed: Nov. 4, 2005

(65) Prior Publication Data

US 2006/0112589 A1    Jun. 1, 2006

Related U.S. Application Data

(63) Continuation of application No. PCT/EP2004/010096, filed on Sep. 10, 2004.

(51) Int. Cl.
*F26B 17/00* (2006.01)

(52) U.S. Cl. .................. 34/90; 34/134; 34/210; 34/218; 34/224; 34/242; 159/4.01; 159/23; 239/68; 203/90

(58) Field of Classification Search ............ 34/90, 34/134, 210, 218, 224, 242; 159/4.01, 23; 239/68; 203/90
See application file for complete search history.

(56) References Cited

U.S. PATENT DOCUMENTS

| | | | | |
|---|---|---|---|---|
| 1,547,171 A * | 7/1925 | Huttlin | .................. | 273/407 |
| 2,046,525 A * | 7/1936 | Miller | .................. | 264/234 |
| 2,264,523 A * | 12/1941 | Gustafsson et al. | ......... | 239/340 |
| 2,303,280 A * | 11/1942 | Jenkins | .................. | 239/296 |
| 2,304,857 A * | 12/1942 | Stahl | .................. | 239/300 |
| 2,366,926 A * | 1/1945 | Melton | .................. | 118/63 |
| 2,416,923 A * | 3/1947 | Jenkins | .................. | 239/299 |
| 2,452,858 A * | 11/1948 | Miller | .................. | 264/605 |
| 2,607,193 A * | 8/1952 | Berggren et al. | .............. | 60/748 |
| 2,610,092 A * | 9/1952 | Thompson | .................. | 239/295 |
| 2,613,112 A * | 10/1952 | Fletcher | .................. | 239/430 |
| 2,624,624 A * | 1/1953 | Kirschbaum | ............. | 239/132.5 |
| 2,680,652 A * | 6/1954 | Kooistra | .................. | 239/493 |
| 2,770,583 A * | 11/1956 | Haddad | .................. | 208/167 |
| 2,792,259 A * | 5/1957 | Shallenberg | .................. | 239/90 |
| 2,893,871 A * | 7/1959 | Griffin | .................. | 426/453 |
| 2,953,457 A * | 9/1960 | Sanna | .................. | 426/242 |
| 2,971,250 A * | 2/1961 | Wahlin | .................. | 29/890.143 |
| 3,174,283 A * | 3/1965 | Crocco et al. | .................. | 60/258 |

(Continued)

FOREIGN PATENT DOCUMENTS

EP    109071 A1 *    5/1984

(Continued)

OTHER PUBLICATIONS

PCT—Notification of Transmittal of Translation of the International Preliminary Report on Patentability, Mar. 13, 2007 (6).

*Primary Examiner*—Stephen Michael Gravini
(74) *Attorney, Agent, or Firm*—St. Onge Steward Johnston & Reens LLC

(57) ABSTRACT

An apparatus for treating particulate material has a process chamber for receiving and treating the material. A bottom is composed of a plurality of overlapping guide plates which are placed one above the other and between which annular slots for process air to pass through are formed. An annular-gap nozzle is arranged centrally in the bottom, the orifice of this annular-gap nozzle being designed in such a way that a planar spray pancake which runs approximately parallel to the bottom plane can be sprayed.

12 Claims, 2 Drawing Sheets

U.S. PATENT DOCUMENTS

Figure 1:
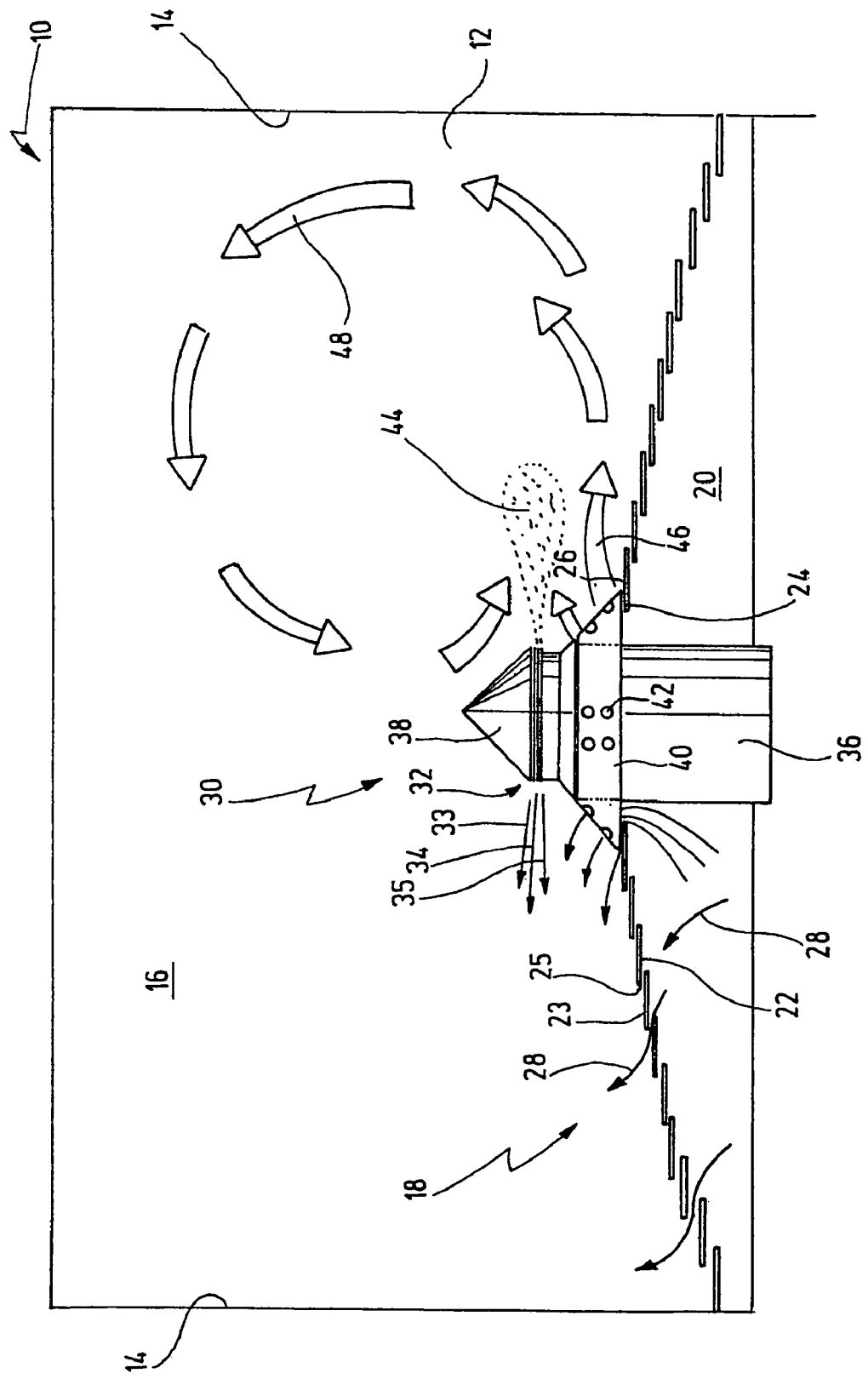

| | | | | |
|---|---|---|---|---|
| 3,187,944 | A * | 6/1965 | Stock | 222/25 |
| 3,237,870 | A * | 3/1966 | McCartney et al. | 239/424 |
| 3,276,844 | A * | 10/1966 | Davison et al. | 422/111 |
| 3,278,125 | A * | 10/1966 | Lorzing, Jr. et al. | 239/405 |
| 3,292,868 | A * | 12/1966 | McCartney et al. | 239/422 |
| 3,309,027 | A * | 3/1967 | Chadwick et al. | 239/406 |
| 3,328,894 | A * | 7/1967 | Smith, Jr. | 34/583 |
| 3,343,814 | A * | 9/1967 | Mund | 366/103 |
| 3,382,129 | A * | 5/1968 | Hampshire | 156/433 |
| 3,401,888 | A * | 9/1968 | Sutter | 239/568 |
| 3,425,634 | A * | 2/1969 | Mutchler | 239/405 |
| 3,493,462 | A * | 2/1970 | Bunting, Jr. et al. | 442/405 |
| 3,504,893 | A * | 4/1970 | Hoshi et al. | 239/488 |
| 3,508,308 | A * | 4/1970 | Bunting, Jr. et al. | 28/104 |
| 3,540,653 | A * | 11/1970 | Fabre | 239/697 |
| 3,672,188 | A * | 6/1972 | Geschka et al. | 68/12.15 |
| 3,696,780 | A * | 10/1972 | Fritzsche | 118/69 |
| 3,732,086 | A * | 5/1973 | Heyne | 65/28 |
| 3,799,716 | A * | 3/1974 | Salts | 425/104 |
| 3,856,036 | A * | 12/1974 | Drews et al. | 137/216.1 |
| 3,866,567 | A * | 2/1975 | Fritzschz | 118/69 |
| 3,874,092 | A * | 4/1975 | Huttlin | 34/130 |
| 3,908,933 | A * | 9/1975 | Goss et al. | 244/3.21 |
| 3,923,253 | A * | 12/1975 | Stewart | 239/463 |
| 3,936,577 | A * | 2/1976 | Christini et al. | 428/614 |
| 3,939,238 | A * | 2/1976 | Salts | 264/71 |
| 3,998,714 | A * | 12/1976 | Armstrong | 210/754 |
| 4,015,366 | A * | 4/1977 | Hall, III | 47/1.43 |
| RE29,285 | E * | 6/1977 | Christini et al. | 428/426 |
| 4,035,296 | A * | 7/1977 | Armstrong | 210/151 |
| 4,035,301 | A * | 7/1977 | Armstrong | 210/220 |
| 4,045,347 | A * | 8/1977 | Armstrong | 210/199 |
| 4,159,131 | A * | 6/1979 | Huttlin | 285/24 |
| 4,184,220 | A * | 1/1980 | Coyle | 15/104.2 |
| 4,204,955 | A * | 5/1980 | Armstrong | 210/760 |
| 4,313,569 | A * | 2/1982 | Burke | 239/333 |
| 4,320,089 | A * | 3/1982 | Huttlin | 422/140 |
| 4,320,584 | A * | 3/1982 | Huttlin | 34/586 |
| RE31,023 | E * | 9/1982 | Hall, III | 405/37 |
| 4,358,057 | A * | 11/1982 | Burke | 239/333 |
| 4,392,777 | A * | 7/1983 | Huttlin | 415/131 |
| 4,434,049 | A * | 2/1984 | Dean et al. | 208/153 |
| 4,444,810 | A * | 4/1984 | Huttlin | 427/212 |
| 4,456,181 | A * | 6/1984 | Burnham | 239/403 |
| 4,463,703 | A * | 8/1984 | Huttlin | 118/19 |
| 4,545,792 | A * | 10/1985 | Huttlin | 96/320 |
| 4,587,744 | A * | 5/1986 | Huttlin | 34/588 |
| 4,645,520 | A * | 2/1987 | Huttlin | 55/287 |
| 4,657,773 | A * | 4/1987 | Mueller | 427/4 |
| 4,674,198 | A * | 6/1987 | Huttlin | 34/135 |
| 4,685,809 | A * | 8/1987 | Huttlin | 366/101 |
| 4,697,356 | A * | 10/1987 | Huttlin | 34/581 |
| 4,736,895 | A * | 4/1988 | Huttlin | 241/40 |
| 4,815,660 | A * | 3/1989 | Boger | 239/8 |
| 4,838,487 | A * | 6/1989 | Schneider | 239/223 |
| 4,934,595 | A * | 6/1990 | Reimer | 239/8 |
| 4,934,651 | A * | 6/1990 | Nowicki | 251/54 |
| 4,952,325 | A * | 8/1990 | Clifford | 210/741 |
| 4,953,365 | A * | 9/1990 | Lang et al. | 62/381 |
| 4,969,602 | A * | 11/1990 | Scholl | 239/298 |
| 4,970,804 | A * | 11/1990 | Huttlin | 34/589 |
| 4,989,790 | A * | 2/1991 | Martin et al. | 239/483 |
| 5,040,310 | A * | 8/1991 | Huttlin | 34/587 |
| RE33,767 | E * | 12/1991 | Christini et al. | 428/544 |
| 5,085,170 | A * | 2/1992 | Huttlin | 118/303 |
| 5,087,349 | A * | 2/1992 | Goelzer et al. | 208/113 |
| 5,145,650 | A * | 9/1992 | Huttlin | 422/143 |
| 5,158,235 | A * | 10/1992 | Johnson | 239/570 |
| 5,178,652 | A * | 1/1993 | Huttlin | 95/279 |
| 5,215,253 | A * | 6/1993 | Saidman et al. | 239/61 |
| 5,228,600 | A * | 7/1993 | Steijns et al. | 222/153.14 |
| 5,282,321 | A * | 2/1994 | Huttlin | 34/594 |
| 5,282,573 | A * | 2/1994 | Reimer | 239/85 |
| 5,305,716 | A * | 4/1994 | Huttlin | 123/18 R |
| 5,400,966 | A * | 3/1995 | Weaver et al. | 239/2.2 |
| 5,405,090 | A * | 4/1995 | Greene et al. | 239/708 |
| 5,427,317 | A * | 6/1995 | Huttlin | 239/422 |
| 5,615,696 | A * | 4/1997 | Lawler | 134/104.2 |
| 5,639,024 | A * | 6/1997 | Mueller et al. | 239/8 |
| 5,688,331 | A * | 11/1997 | Aruga et al. | 118/725 |
| 5,727,739 | A * | 3/1998 | Hamilton | 239/600 |
| 5,743,969 | A * | 4/1998 | Lawler | 134/10 |
| 5,934,555 | A * | 8/1999 | Dobbeling et al. | 239/11 |
| 6,009,847 | A * | 1/2000 | Huttlin | 123/241 |
| 6,045,061 | A * | 4/2000 | Huttlin | 239/424 |
| 6,129,290 | A * | 10/2000 | Nikkanen | 239/2.2 |
| 6,161,769 | A * | 12/2000 | Kircher et al. | 239/2.2 |
| 6,193,172 | B1 * | 2/2001 | Soule et al. | 239/468 |
| 6,230,986 | B1 * | 5/2001 | Vacher et al. | 239/297 |
| 6,311,473 | B1 * | 11/2001 | Benjamin et al. | 60/776 |
| 6,358,290 | B1 * | 3/2002 | Huttlin | 55/283 |
| 6,367,165 | B1 * | 4/2002 | Huttlin | 34/582 |
| 6,379,614 | B1 * | 4/2002 | Sergio et al. | 422/28 |
| 6,431,139 | B1 * | 8/2002 | Huttlin | 123/241 |
| 6,521,180 | B2 * | 2/2003 | Sergio et al. | 422/28 |
| 6,533,954 | B2 * | 3/2003 | Mansour et al. | 216/100 |
| 6,550,696 | B2 * | 4/2003 | Mansour et al. | 239/399 |
| 6,649,384 | B2 * | 11/2003 | Walsh et al. | 435/178 |
| 6,718,770 | B2 * | 4/2004 | Laing et al. | 60/740 |
| 6,730,167 | B2 * | 5/2004 | Shutic et al. | 118/309 |
| 6,740,162 | B2 * | 5/2004 | Huttlin | 118/303 |
| RE38,526 | E * | 6/2004 | Hansinger et al. | 239/3 |
| 6,746,001 | B1 * | 6/2004 | Sherikar | 261/62 |
| 6,769,969 | B1 * | 8/2004 | Duescher | 451/59 |
| 6,782,947 | B2 * | 8/2004 | de Rouffignac et al. | 166/245 |
| 6,827,289 | B2 * | 12/2004 | Filicicchia et al. | 239/124 |
| 6,877,555 | B2 * | 4/2005 | Karanikas et al. | 166/245 |
| 6,880,633 | B2 * | 4/2005 | Wellington et al. | 166/245 |
| 6,898,869 | B2 * | 5/2005 | Huttlin | 34/585 |
| 6,898,926 | B2 * | 5/2005 | Mancini | 60/39.094 |
| 6,898,938 | B2 * | 5/2005 | Mancini et al. | 60/748 |
| 6,915,850 | B2 * | 7/2005 | Vinegar et al. | 166/272.2 |
| 6,918,442 | B2 * | 7/2005 | Wellington et al. | 166/245 |
| 6,918,443 | B2 * | 7/2005 | Wellington et al. | 166/245 |
| 6,923,257 | B2 * | 8/2005 | Wellington et al. | 166/245 |
| 6,929,067 | B2 * | 8/2005 | Vinegar et al. | 166/302 |
| 6,932,155 | B2 * | 8/2005 | Vinegar et al. | 166/245 |
| 6,948,562 | B2 * | 9/2005 | Wellington et al. | 166/272.1 |
| 6,949,141 | B2 * | 9/2005 | Huttlin | 118/303 |
| 6,951,247 | B2 * | 10/2005 | de Rouffignac et al. | 166/245 |
| 6,964,300 | B2 * | 11/2005 | Vinegar et al. | 166/245 |
| 6,966,374 | B2 * | 11/2005 | Vinegar et al. | 166/272.3 |
| 6,969,123 | B2 * | 11/2005 | Vinegar et al. | 299/3 |
| 6,981,548 | B2 * | 1/2006 | Wellington et al. | 166/245 |
| 6,991,032 | B2 * | 1/2006 | Berchenko et al. | 166/245 |
| 6,991,036 | B2 * | 1/2006 | Sumnu-Dindoruk et al. | 166/302 |
| 6,991,045 | B2 * | 1/2006 | Vinegar et al. | 175/45 |
| 6,994,169 | B2 * | 2/2006 | Zhang et al. | 166/302 |
| 6,997,518 | B2 * | 2/2006 | Vinegar et al. | 299/5 |
| 7,004,247 | B2 * | 2/2006 | Cole et al. | 166/60 |
| 7,004,251 | B2 * | 2/2006 | Ward et al. | 166/245 |
| 7,011,154 | B2 * | 3/2006 | Maher et al. | 166/245 |
| 7,013,972 | B2 * | 3/2006 | Vinegar et al. | 166/257 |
| 7,014,670 | B2 * | 3/2006 | Shutic et al. | 55/315 |
| 7,021,562 | B2 * | 4/2006 | Mansour et al. | 239/403 |
| 7,028,483 | B2 * | 4/2006 | Mansour et al. | 60/748 |
| 7,032,660 | B2 * | 4/2006 | Vinegar et al. | 166/245 |
| 7,040,397 | B2 * | 5/2006 | de Rouffignac et al. | 166/245 |
| 7,040,398 | B2 * | 5/2006 | Wellington et al. | 166/245 |
| 7,040,399 | B2 * | 5/2006 | Wellington et al. | 166/245 |
| 7,040,400 | B2 * | 5/2006 | de Rouffignac et al. | 166/245 |
| 7,051,807 | B2 * | 5/2006 | Vinegar et al. | 166/245 |
| 7,051,808 | B1 * | 5/2006 | Vinegar et al. | 166/250.1 |

| Patent No. | Date | Inventor | Class |
|---|---|---|---|
| 7,051,811 B2 * | 5/2006 | de Rouffignac et al. | 166/302 |
| 7,051,954 B2 * | 5/2006 | Gerstner | 239/398 |
| 7,055,600 B2 * | 6/2006 | Messier et al. | 166/250.01 |
| 7,063,145 B2 * | 6/2006 | Veenstra et al. | 166/250.01 |
| 7,066,254 B2 * | 6/2006 | Vinegar et al. | 166/245 |
| 7,066,257 B2 * | 6/2006 | Wellington et al. | 166/272.2 |
| 7,077,198 B2 * | 7/2006 | Vinegar et al. | 166/245 |
| 7,077,199 B2 * | 7/2006 | Vinegar et al. | 166/250.01 |
| 7,083,122 B2 * | 8/2006 | Mansour et al. | 239/399 |
| 7,086,465 B2 * | 8/2006 | Wellington et al. | 166/272.1 |
| 7,090,013 B2 * | 8/2006 | Wellington | 166/267 |
| 7,096,942 B1 * | 8/2006 | de Rouffignac et al. | 166/245 |
| 7,100,994 B2 * | 9/2006 | Vinegar et al. | 299/7 |
| 7,104,319 B2 * | 9/2006 | Vinegar et al. | 166/245 |
| 7,114,566 B2 * | 10/2006 | Vinegar et al. | 166/256 |
| 7,128,153 B2 * | 10/2006 | Vinegar et al. | 166/285 |
| 7,156,176 B2 * | 1/2007 | Vinegar et al. | 166/302 |
| 7,156,260 B2 * | 1/2007 | Hayduk | 222/145.5 |
| 7,165,615 B2 * | 1/2007 | Vinegar et al. | 166/302 |
| 7,168,183 B2 * | 1/2007 | Huttlin | 34/579 |
| 7,182,221 B2 * | 2/2007 | Hanna et al. | 222/145.5 |
| 7,211,169 B2 * | 5/2007 | Noble | 156/583.1 |
| 7,213,383 B2 * | 5/2007 | Walker et al. | 53/329.2 |
| 7,222,753 B2 * | 5/2007 | Hayduk | 222/145.5 |
| 7,225,866 B2 * | 6/2007 | Berchenko et al. | 166/245 |
| RE39,767 E * | 8/2007 | Soule et al. | 239/468 |
| 7,325,750 B2 * | 2/2008 | Shutic et al. | 239/1 |
| 7,331,542 B2 * | 2/2008 | Cocciadiferro et al. | 242/597 |
| 7,341,632 B2 * | 3/2008 | Noble | 118/317 |
| 7,386,969 B2 * | 6/2008 | Hayduk | 53/459 |
| 7,435,064 B2 * | 10/2008 | Huttlin | 418/35 |
| 7,461,691 B2 * | 12/2008 | Vinegar et al. | 166/60 |
| 7,490,737 B2 * | 2/2009 | Cocciadiferro et al. | 222/145.5 |
| 2001/0048036 A1 * | 12/2001 | Mansour et al. | 239/8 |
| 2001/0050318 A1 * | 12/2001 | Mansour et al. | 239/403 |
| 2002/0037236 A1 * | 3/2002 | Sergio et al. | 422/33 |
| 2002/0044898 A1 * | 4/2002 | Sergio et al. | 422/300 |
| 2002/0078883 A1 * | 6/2002 | Shutic et al. | 118/50 |
| 2002/0153436 A1 * | 10/2002 | Selic | 239/585.1 |
| 2003/0038192 A1 * | 2/2003 | Shutic et al. | 239/690.1 |
| 2003/0155325 A1 * | 8/2003 | Mansour et al. | 216/2 |
| 2004/0083980 A1 * | 5/2004 | Harding | 119/60 |
| 2004/0124282 A1 * | 7/2004 | Mansour et al. | 239/548 |
| 2005/0022483 A1 * | 2/2005 | Shutic et al. | 55/337 |
| 2005/0103019 A1 * | 5/2005 | Mansour et al. | 60/776 |
| 2005/0126476 A1 * | 6/2005 | Shutic et al. | 118/308 |
| 2005/0178851 A1 * | 8/2005 | Shutic et al. | 239/124 |
| 2006/0112589 A1 * | 6/2006 | Huttlin | 34/585 |
| 2006/0137315 A1 * | 6/2006 | Shutic et al. | 55/459.1 |
| 2007/0234586 A1 * | 10/2007 | Huettlin | 34/77 |
| 2007/0236693 A1 * | 10/2007 | Prociw et al. | 356/336 |
| 2007/0242871 A1 * | 10/2007 | Prociw et al. | 382/141 |
| 2008/0264784 A1 * | 10/2008 | Pecher et al. | 204/298.07 |
| 2009/0159461 A1 * | 6/2009 | McCutchen et al. | 205/751 |

FOREIGN PATENT DOCUMENTS

| | | | |
|---|---|---|---|
| EP | 146680 | A1 * | 7/1985 |
| EP | 172530 | A2 * | 2/1986 |
| EP | 331111 | A1 * | 9/1989 |
| EP | 378110 | A1 * | 7/1990 |

* cited by examiner

APPARATUS FOR TREATING PARTICULATE MATERIAL

FIELD OF INVENTION

This application is a continuation of pending International Patent Application PCT/EP2004/010096 filed on Sep. 10, 2004 which designates the United States.

BACKGROUND OF THE INVENTION

The invention relates to an apparatus for treating particulate material, having a process chamber which is intended for receiving and treating the material and has a bottom which is composed of a plurality of overlapping guide plates which are placed one above the other and between which annular slots are formed, via which process air having an essentially horizontal component motion directed radially outward can be introduced.

Such an apparatus has been disclosed, for example, by DE 102 48 116 B3.

Such known apparatuses serve to dry, granulate or coat particulate material. A gaseous medium, "process air", is introduced into the process chamber via the bottom and enters the process chamber in an approximately horizontally oriented manner through the numerous slots between the overlapping guide plates. Due to overlapping, annular guide plates, between which numerous slots are formed, a flow of process air directed radially from inside to outside forms in the process chamber and is deflected upward by the wall of the process chamber. The material to be treated is entrained in the process, but falls centrally downward on account of the gravitational force and again strikes the air cushion of the process air. If a certain extensive component is imposed on the process air, a toroidally revolving swirl flow ring gradually forms.

If larger agglomerates are to be formed from powders as fine as dust, that is to say if the material is to be granulated, a sticky medium is sprayed toward the toroidal ring via nozzles. In DE 102 48 116 B3 mentioned at the beginning, for example, spray nozzles directed obliquely upward are inserted into the wall of the container which encloses the process chamber.

During coating, a coating layer is to be applied as uniformly as possible to a larger body already present, that is to say said coating layer is to be sprayed on.

Various configurations of nozzles are known, the common feature of which is that a usually liquid or also particulate treatment substance is sprayed by means of spray air to form a fine mist. To this end, it has become known, for example, to expel the liquid under high pressure from a slot-shaped nozzle orifice and to spray it through spray-air orifices, whether on one side or on both sides of the liquid gap.

DE 102 32 863 A1 has disclosed an atomizing nozzle which has flow passages which are annular in cross section. Depending on the spray angle and looping angle, radiate, conical or more or less planar spray pancakes are produced. At a spray angle of 180° and a looping angle of 360° a virtually planar spray pancake is produced.

In this technology, which is widely used in the pharmaceutical field of application, it is attempted to achieve a result which is as uniform as possible, i.e. to achieve granulates with a very narrow grain size distribution, and to achieve during the coating a coating layer which is as uniform as possible, i.e. in particular a coating layer of identical thickness, at all particles of the charge which are contained in the apparatus. A considerable problem consists in the fact that material particles which wander around in an uncontrolled manner and are wetted with the moist and usually sticky spray liquid adhere to one another to form unwanted agglomerates.

Therefore precisely defined flow conditions which permit an optimum treatment result are desired in the toroidally rotating material band. In particular, it is desired that, after the spraying, the particles assume a flight path in which they move away from one another where possible and not toward one another in order to prevent undesirable agglomerates.

It is therefore the object of the present invention to provide for an improvement in such apparatuses for the treatment of particulate material to the effect that a harmonious sequence of movement with an optimum treatment result can be achieved.

SUMMARY OF THE INVENTION

According to the invention, the object is achieved in that, in an apparatus of the type mentioned at the beginning, an annular-gap nozzle is arranged centrally in the bottom, the orifice of this annular-gap nozzle being designed in such a way that a planar spray pancake which runs approximately parallel to the bottom plane can be sprayed.

The combination of such an annular-gap nozzle with a bottom of annular guide plates having a flow of process air directed from inside to outside now leads surprisingly to an especially harmonious guidance of air and material. The process air discharging through the annular slots forms an air cushion which glides radially from inside to outside over the bottom and leads the material to be treated radially outward into an increasingly larger available space; the particles thus first of all move away from one another.

The process air directed upward on the wall carries the material particles along with it vertically upward. These material particles separate from the process air flowing off, are moved in a radially inwardly directed manner toward the center and, on account of the gravitational force, fall downward approximately centrally in the center onto the cushion of process air passing through the bottom. Due to the central provision of the annular-gap nozzle with the planar spray pancake sprayed from said annular-gap nozzle, the material falling down can be sprayed uniformly and can then immediately be moved radially outward in a radiated manner, that is to say the material particles can be moved away from one another. The material particles are therefore sprayed in a very specific manner by the spray pancake when falling down, are cushioned by the process air cushion and are moved radially outward. After leaving the spray pancake, the further path directed horizontally radially outward, with the subsequent movement rising vertically upward and the movement returning again to the center, is available in order to dry and accordingly solidify the sprayed particles by means of the process air before they strike the spray pancake again. Due to the 360° looping of the spray pancake, all the material falling down centrally can be sprayed uniformly by the spray liquid.

It has now been surprisingly found that a harmonious uniform optimum treatment of the material can be achieved by this combination. The annular-gap nozzle works "amidships" and "underbed". The material falling onto the spray pancake is received by the process air cushion and is treated in an especially harmonious and uniform manner.

Even in the case of very large test batches up to 650 kg, a perfect granulating, coating and drying process is achieved. The air cushion on the bottom side keeps the bottom surface completely free of sprayed substance, i.e. all the sprayed substance is fed into the material, so that no spray losses occur, which is extremely important in particular in the pharmaceutical field.

In a further embodiment of the invention, discharge openings for support air are provided between the orifice of the annular-gap nozzle and the bottom lying underneath in order to effect a support cushion on the underside of the spray pancake.

It is generally known that a certain vacuum is produced in the immediate region of a nozzle orifice, and this vacuum results in accumulations of material next to the spray orifice. In the case of the spray pancake mentioned at the beginning, no problem is to be seen on its top side in this respect, since of course the material particles fall down centrally and are directed away horizontally. On the underside of the spray pancake, however, such vacuum zones could gradually cause particle accumulations. Support air is provided by the provision of the additional discharge openings, this region on the underside in the region of the orifice of the annular-gap nozzle being "blown free" by said support air. A further additional effect is that the support air can actually support the sprayed planar spray pancake on its underside, that is to say said support air prevents the spray pancake from undesirably moving downward on account of the gravitational force or on account of the spray cone forming in cross section. This rules out the possibility of spray losses or of the sticky materials being deposited on the top side of the bottom.

In a further embodiment of the invention, the support air is provided from the annular-gap nozzle itself and/or by process air.

These measures enable the support air to be brought about in many different ways. Discharge openings may be provided on the annular-gap nozzle itself, via which discharge openings some of the spray air discharges in order to help to form the support air. In addition or alternatively, some of the process air which flows through the bottom can be directed in the direction of the underside of the spray pancake and can thus help to form the support air.

In a further embodiment of the invention, the annular-gap nozzle has an approximately conical head, and the orifice runs along a circular area of a conic section.

This measure has the advantage that, by means of the cone, the material particles moving vertically from top to bottom are fed uniformly, smoothly and specifically onto the spray pancake which is sprayed from the circular spray gap in the bottom end of the cone.

In a further embodiment of the invention, a frustoconical wall is provided in the region between the orifice and the bottom lying underneath, this frustoconical wall having through-openings for support air.

This measure has the advantage that the abovementioned harmonious deflecting movement is maintained by the continuation via the frustum, and support air can discharge through the through-openings in this region and provides for the corresponding support on the underside of the spray pancake.

In a further embodiment of the invention, an annular slot for process air to pass through is formed between the underside of the frustoconical wall.

This measure has the advantage that the transfer of the material particles to the air cushion of the bottom can be controlled especially effectively and, starting in a specific manner, can be carried out directly in the region below the nozzle.

In a further embodiment of the invention, an orifice of a feed for a substance is arranged above the annular-gap nozzle.

It has been found that an additional substance can be fed very effectively on account of the harmonious flow of the selected combination of annular gaps and annular-gap nozzle. It is therefore possible, for example, to directly feed a powder centrally onto the spray pancake when the latter is being formed, so that a powder can be put in a firmly adhering manner onto the surface, made sticky by the nozzle, of the material to be treated. As a result, a rapid increase in the layer thickness during the coating can be achieved. This is not the only advantage. A further considerable advantage consists in the fact that, for example, it is possible to feed an active substance which is sensitive to moisture and therefore cannot be processed in a suspension or in a solution and sprayed through the annular-gap nozzle. In this case, the annular-gap nozzle sprays only the sticky medium; the actual active substance is fed centrally as powder. This further feeding, which of course from the fluidic point of view is an additional parameter to be taken into account, can therefore be carried out, since a highly defined and harmonious flow can be achieved by the abovementioned combination.

In a further embodiment of the invention, guide elements are arranged between the annular guide plates, these guide elements additionally imposing an extensive flow component on the process air passing through.

This measure known per se has the advantage that the corresponding extensive component motion can be imposed by these guide elements in order to form the toroidally rotating band of uniformly swirled material particles, which as a result can uniformly strike the planar spray pancake.

It goes without saying that the abovementioned features and the features still to be explained below can be used not only in the specified combination but also in other combinations or on their own without departing from the scope of the present invention.

BRIEF DESCRIPTION OF THE DRAWINGS

The invention is described in more detail below with reference to a few selected exemplary embodiments in connection with the attached drawings, in which:

FIG. 1 shows a highly schematic diametral cross section through an apparatus for treating particulate material, and FIG. 2 shows a corresponding section with an additional feed for a further substance.

DETAIL DESCRIPTION OF THE DRAWINGS

An apparatus shown in FIG. 1 for treating particulate material is provided overall with the reference numeral 10.

The apparatus 10 has a container 12 with an upright cylindrical wall 14. This wall 14 encloses a corresponding process chamber 16.

The process chamber 16 has a bottom 18, below which an inflow chamber 20 is located.

As disclosed, for example by DE 192 48 116 B3 mentioned at the beginning, the bottom 18 is composed of a total of ten annular guide plates situated one above the other. The ten guide plates are set one above the other in such a way that an outermost annular plate connected to the wall 14 forms a lowermost annular plate, on which the further nine inner annular plates are then placed, these nine inner annular plates partly overlapping the respective annular plate underneath.

For the sake of clarity, only some of the guide plates are provided with reference numerals, for example the two guide plates 22 and 23 lying one above the other. By this placing one above the other and by the spacing, an annular slot 25 is formed in each case between two guide plates, through which slot 25 process air 28 having an essentially horizontally directed component motion can pass through the bottom 18, as is of course known per se. Inserted from below in the central uppermost inner guide plate 24 in its central opening is an annular-gap nozzle 30. The annular-gap nozzle 30 has an orifice 32, which has a total of three orifice gaps 33, 34 and 35. All three orifice gaps 33, 34 and 35 are oriented in such a way that they spray approximately parallel to the bottom 18, that is to say approximately horizontally with a looping angle of 360°. Spray air is forced out via the top gap 33 and the lowest gap 35, and the liquid to be sprayed is forced out through the middle gap 34.

The annular-gap nozzle 30 has a rod-shaped body 36 which extends downward and contains the corresponding passages and feed lines, as is known per se. The annular-gap nozzle may be designed, for example, like the atomizing nozzle from DE 102 32 863 A1.

This annular-gap nozzle may be formed, for example, with a "rotary annular gap", in which the walls of the passage through which the liquid is sprayed rotate relative to one another in order to rule out clogging or lumping, so that spraying from the gap 34 can be effected uniformly over the entire looping angle of 360°. With respect to the longitudinal axis of the body 36 of the annular-gap nozzle 30, there is therefore a spray angle of 180°.

The annular-gap nozzle 30 has a conical head 38 above the orifice 32.

In the region below the orifice 32, there is a frustoconical wall 40 which has numerous openings 42. As can be seen from FIG. 1, the underside of the frustoconical wall 40 rests on the innermost guide plate 24, to be precise in such a way that a slot 26 through which process air can pass is formed between the underside of the frustoconical wall 40 and the guide plate 24 lying underneath and partly overlapping with said wall 40.

The flow conditions which form in the run-in state are shown in the right-hand half of FIG. 1.

A planar spray pancake 44 discharges from the orifice 32. Due to the air which passes through the openings 42 in the frustoconical wall 40 and which may be, for example, process air, a support air flow 46 forms on the underside of the spray pancake 44. Due to the process air 28 which passes through the numerous slots 25, 26, a radial flow forms in the direction of the wall 14 and is deflected upward by the latter, as shown by an arrow 48. The process air and the material to be treated now separate from one another, the process air is drawn off through outlets, the swirled material is moved radially inward and falls vertically downward in the direction of the conical head 38 of the annular-gap nozzle 30 on account of the gravitational force. The material falling down is smoothly diverted there and is directed onto the top side of the spray pancake 44 and is treated there with the sprayed medium. The sprayed particles in the spray pancake move away from one another, since of course a considerably larger space is available to the particles after leaving the annular orifice 32. In the region of the spray pancake, the material particles to be treated collide with liquid particles and, remaining in this direction of movement, are moved away from one another and in the process are treated very uniformly and harmoniously with process air, that is to say they are dried.

Figure 2:
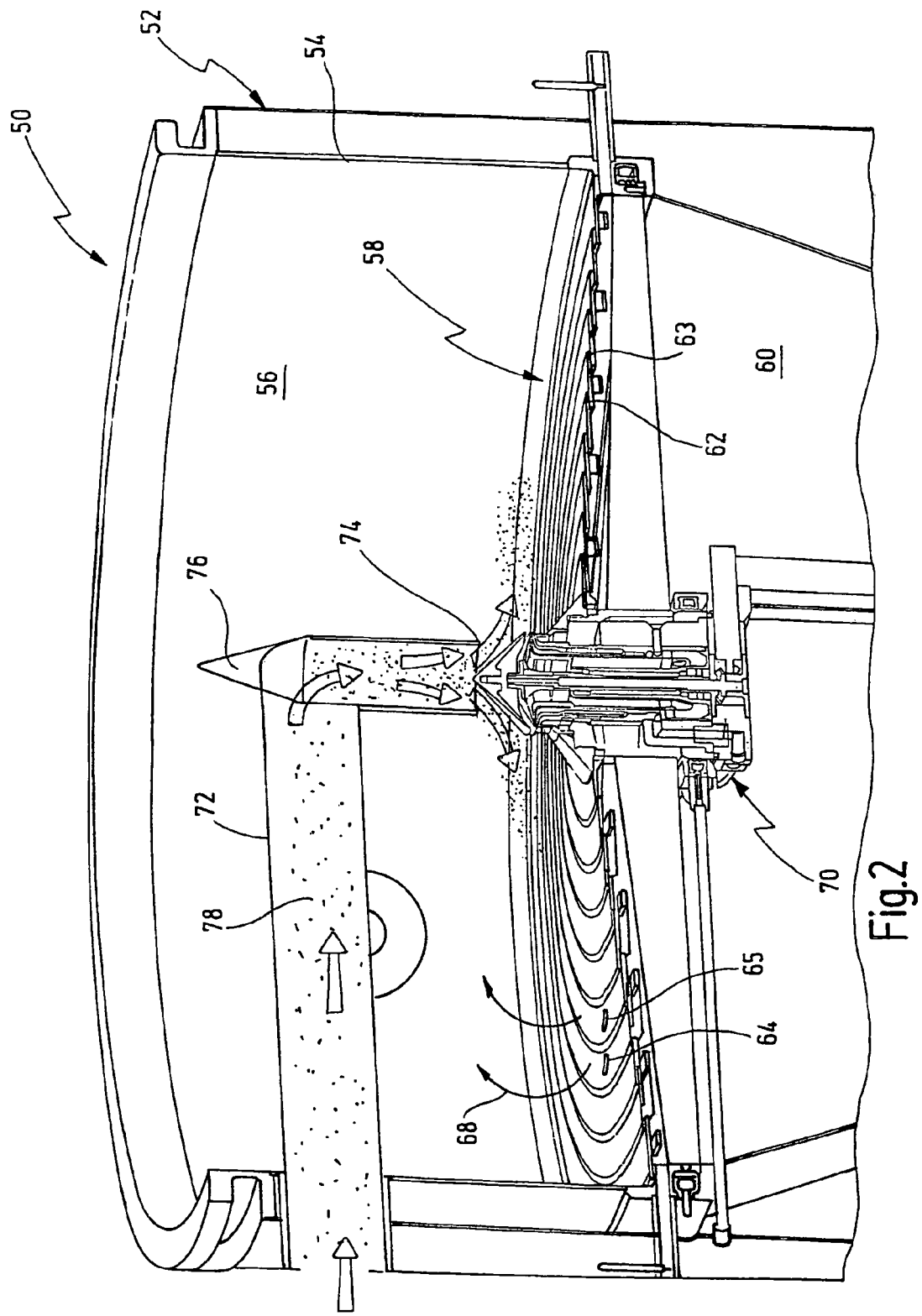

A section comparable with the section in FIG. 1 is shown in perspective in FIG. 2, the apparatus shown there being provided overall with the reference numeral 50. Here, too, there is a container 52 which has a cylindrical upright wall 54 in which a process chamber 56 is defined. As described above in connection with FIG. 1, the bottom 58 is composed of ten guide plates correspondingly placed one above the other, only the two guide plates 62 and 63, for example, being designated here. The inflow chamber 60 is then again located below the bottom 58.

It is shown here that guide elements 64 and 65 are arranged between the guide plates, these guide elements 64 and 65 leading to a situation in which not only does the process air passing though between the guide plates 62 and 63 flow exactly radially outward, but a certain extensive component motion is imposed on said process air, as shown by the arrow 68.

Here, too, a corresponding annular-gap nozzle 70 as described above is again arranged centrally. A feed 72, for example a laterally fed pipe, is arranged centrally above the annular-gap nozzle, the orifice 74 of the feed 72 lying exactly coaxially centrally above the annular-gap nozzle 70. The position of the orifice can be adjusted vertically.

This makes it possible, for example, to bring a solid in the form of a powder 78 onto the top side of the planar spray pancake sprayed from the annular-gap nozzle 70.

In both configurations mentioned, the annular-gap nozzle 30 or 70, respectively, is designed in such a way that it can be removed from the bottom from below even during operation, for example in order to check for a malfunction or the like. Before removal, the feed of the spray liquid is of course stopped; however, it is still possible to circulate the material in the apparatus 10 or 50, since a process-air column rising upward forms in the central hole, so that it is impossible for material particles to fall through this opening. This is again a consequence of the highly defined harmonious swirling movement within the limits of the toroidally rotating band.

What is claimed is:

1. An apparatus for treating particulate material, comprising:
    a process chamber which is intended for receiving and treating a material,
    said process chamber having a horizontal bottom which is composed of a plurality of overlapping annular guide plates, which are placed one above the other and between which overlapping annular guide plates annular slots are formed, via which annular slots a process air having an essentially horizontal component motion directed radially outward can be introduced into said process chamber, and
    an annular-gap nozzle being arranged centrally in said bottom, an orifice of said annular-gap nozzle having orifice gaps oriented in such a way that they spray approximately horizontally with a looping angle of 360° such that a planar spray pancake which runs approximately parallel to a bottom plane can be sprayed,
    a central feed for a substance arranged above said annular-gap nozzle, said feed having a discharge orifice arranged above said annular-gap nozzle, wherein said feed and said discharge orifice can be adjusted vertically.

2. The apparatus of claim 1, wherein discharge openings are provided between said orifice of said annular-gap nozzle and said bottom disposed underneath of said orifice, said discharge openings serving for discharging a support air in order to effect a support cushion on an underside of said spray pancake.

3. The apparatus of claim 2, wherein said support air discharged from said discharge openings is provided from said annular-gap nozzle.

4. The apparatus of claim 2, wherein said support air discharged by said discharge openings is provided by said process air.

5. The apparatus of claim 2, wherein said support air discharged from said discharge openings is provided from said annular-gap nozzle and by said process air.

6. The apparatus of claim 1, wherein said annular-gap nozzle has an approximately conical head, and wherein said orifice of said annular-gap nozzle runs along a circular circumferential line of said conical head.

7. The apparatus of claim 6, wherein a frustoconical wall is disposed between said orifice of said annular-gap nozzle and said bottom lying underneath, said frustoconical wall having openings for discharging a support air for supporting said planar spray pancake.

8. The apparatus of claim 7, wherein an annular slot for passing process air is formed at an underside of said frustoconical wall.

9. The apparatus of claim 1, wherein guide elements are arranged between said annular guide plates, said guide elements additionally imposing a flow component on said process air passing through said guide plates.

10. The apparatus of claim 1, wherein said orifice of said feed lies exactly coaxially above the annular-gap nozzle.

11. The apparatus of claim 1, wherein a solid is introduced through said feed.

12. The apparatus of claim 1, wherein said solid can be a powder.

* * * * *

UNITED STATES PATENT AND TRADEMARK OFFICE
CERTIFICATE OF CORRECTION

| | | |
|---|---|---|
| PATENT NO. | : 7,802,376 B2 | Page 1 of 1 |
| APPLICATION NO. | : 11/267518 | |
| DATED | : September 28, 2010 | |
| INVENTOR(S) | : Herbert Hüttlin | |

It is certified that error appears in the above-identified patent and that said Letters Patent is hereby corrected as shown below:

Page 1:

(76) Inventor: should read: Herbert Hüttlin, Rümminger Straße 15, 79539 Lörrach (DE)

Signed and Sealed this

Sixteenth Day of November, 2010

David J. Kappos
*Director of the United States Patent and Trademark Office*